(12) United States Patent
Shelton et al.

(10) Patent No.: US 11,576,568 B2
(45) Date of Patent: Feb. 14, 2023

(54) SELF-ORIENTING IMAGING DEVICE AND METHODS OF USE

(71) Applicant: PhotoniCare, Inc., Champaign, IL (US)

(72) Inventors: Ryan Shelton, Bentonville, AR (US); Wei Kang, Somerville, MA (US)

(73) Assignee: PhotoniCare Inc., Champaign, IL (US)

( * ) Notice: Subject to any disclaimer, the term of this patent is extended or adjusted under 35 U.S.C. 154(b) by 871 days.

(21) Appl. No.: 16/502,171

(22) Filed: Jul. 3, 2019

(65) Prior Publication Data

US 2019/0320887 A1 Oct. 24, 2019

Related U.S. Application Data

(63) Continuation of application No. PCT/US2018/012744, filed on Jan. 8, 2018.

(60) Provisional application No. 62/443,227, filed on Jan. 6, 2017.

(51) Int. Cl.

| | | |
|---|---|---|
| H04N 7/18 | (2006.01) | |
| A61B 1/227 | (2006.01) | |
| A61B 1/00 | (2006.01) | |
| A61B 1/04 | (2006.01) | |
| A61B 5/06 | (2006.01) | |
| A61B 5/00 | (2006.01) | |

(52) U.S. Cl.
CPC .......... *A61B 1/227* (2013.01); *A61B 1/00045* (2013.01); *A61B 1/00057* (2013.01); *A61B 1/00172* (2013.01); *A61B 1/04* (2013.01); *A61B 5/067* (2013.01); *A61B 1/00009* (2013.01); *A61B 5/0035* (2013.01); *A61B 5/0066* (2013.01)

(58) Field of Classification Search
CPC .................................................... A61B 1/227
USPC ........................................................ 382/296
See application file for complete search history.

(56) References Cited

U.S. PATENT DOCUMENTS

| | | | | |
|---|---|---|---|---|
| 5,919,130 A | * | 7/1999 | Monroe | A61B 1/042 600/156 |
| 6,111,645 A | * | 8/2000 | Tearney | A61B 1/00172 356/484 |
| 6,122,538 A | | 9/2000 | Sliwa, Jr. et al. | 600/407 |
| 6,141,031 A | * | 10/2000 | Nowak | H04N 1/1135 347/246 |

(Continued)

FOREIGN PATENT DOCUMENTS

| | | | | |
|---|---|---|---|---|
| CN | 104737530 A | | 6/2015 | |
| EP | 1142529 | | 10/2001 | ............... A61B 1/00 |

(Continued)

OTHER PUBLICATIONS

European Search Report issued in corresponding foreign application, EP 18736638.0, pp. 1-7 (dated Nov. 2, 2020).

(Continued)

*Primary Examiner* — Leron Beck
(74) *Attorney, Agent, or Firm* — J. Peters Paredes; Amin Talati Wasserman LLP (57) ABSTRACT

The Self-Orienting Imaging Device and Methods of Use sense the orientation of the handheld imaging, and apply the rotational correction by rotating the image to be displayed. When a scanner is used, the scanning element in the scanner is adjusted, such that the eventual scanning direction remains unchanged referencing the subject anatomy. The self-orienting mechanism for the scanner may be implemented in hardware mechanisms.

16 Claims, 4 Drawing Sheets

(56) References Cited

U.S. PATENT DOCUMENTS

| | | | |
|---|---|---|---|
| 6,471,637 B1 | 10/2002 | Green et al. ................ 600/109 |
| 8,115,934 B2 | 2/2012 | Boppart et al. ............. 356/479 |
| 8,594,757 B2 | 11/2013 | Boppart et al. ............. 600/310 |
| 9,339,649 B2* | 5/2016 | Cushing ............. A61N 1/36038 |
| 9,638,511 B2 | 5/2017 | Boppart et al. .... G01B 9/02091 |
| 9,867,528 B1 | 1/2018 | Boppart et al. ...... A61B 1/2275 |
| 10,278,570 B2 | 5/2019 | Nolan et al. ......... A61B 1/2275 |
| 2004/0097791 A1* | 5/2004 | Tokuda ............. A61B 1/00183 |
| | | 600/173 |
| 2004/0201595 A1* | 10/2004 | Manchester ............. G09G 5/37 |
| | | 345/649 |
| 2005/0077359 A1* | 4/2005 | Boehm ............. G06K 7/10544 |
| | | 235/454 |
| 2008/0159653 A1* | 7/2008 | Dunki-Jacobs .......... A61B 1/04 |
| | | 382/293 |
| 2008/0273755 A1* | 11/2008 | Hildreth ............... G06F 1/1626 |
| | | 345/158 |
| 2009/0040308 A1 | 2/2009 | Temovskiy .................... 348/158 |
| 2009/0185191 A1* | 7/2009 | Boppart ............. A61B 5/6852 |
| | | 356/479 |
| 2009/0306509 A1 | 12/2009 | Pedersen et al. ............. 600/446 |
| 2009/0326556 A1 | 12/2009 | Diolaiti et al. ............... 606/130 |
| 2010/0097444 A1* | 4/2010 | Lablans ............... H04N 13/189 |
| | | 348/46 |
| 2011/0211104 A1* | 9/2011 | Hendriks ............. G02B 26/103 |
| | | 359/201.1 |
| 2012/0310098 A1* | 12/2012 | Popovic ............. A61B 5/1076 |
| | | 600/476 |
| 2013/0016234 A1 | 1/2013 | Silverbrook ............... 348/207.2 |
| 2013/0060131 A1* | 3/2013 | Oghalai ............. A61B 1/00165 |
| | | 600/425 |
| 2013/0338447 A1* | 12/2013 | Gilad-Gilor ......... A61B 5/0002 |
| | | 600/300 |
| 2014/0350379 A1* | 11/2014 | Verdooner ........... A61B 5/0059 |
| | | 600/407 |
| 2014/0375784 A1 | 12/2014 | Massetti ................. A61B 1/05 |
| 2016/0007840 A1* | 1/2016 | Boppart ............... A61B 5/6817 |
| | | 600/188 |
| 2016/0100821 A1 | 4/2016 | Eggers et al. |
| 2016/0239631 A1* | 8/2016 | Wu ........................ G16H 50/50 |
| 2016/0255261 A1* | 9/2016 | Govari .................... A61B 1/04 |
| | | 348/69 |
| 2017/0102231 A1* | 4/2017 | Yahng ............... G01N 21/3586 |
| 2018/0129129 A1* | 5/2018 | Seger ..................... G02B 27/06 |
| 2019/0142258 A1 | 5/2019 | Nolan et al. ......... A61B 1/2275 |
| 2020/0245900 A1* | 8/2020 | Douglas ........... A61B 5/150809 |

FOREIGN PATENT DOCUMENTS

| | | | |
|---|---|---|---|
| JP | 2012528414 A | 11/2012 | |
| WO | WO2007/033326 | 3/2007 | ............... A61B 3/10 |
| WO | 2015196388 A1 | 12/2015 | |
| WO | WO2018/129430 | 7/2018 | ............ A61B 1/227 |
| WO | WO2018/160561 | 9/2018 | ................ G01J 3/45 |

OTHER PUBLICATIONS

International Search Report and Written Opinion issued in corresponding foreign application, PCT/US2018/012744, pp. 1-6 (dated May 4, 2018).

International Preliminary Report on Patentability issued in corresponding foreign application, PCT/US2018/012744, pp. 1-5 (dated Jul. 18, 2019).

* cited by examiner

FIG. 1A

Prior Art

Prior Art

$$\begin{bmatrix} \cos\theta & -\sin\theta & 0 \\ \sin\theta & \cos\theta & 0 \\ 0 & 0 & 1 \end{bmatrix}$$

SELF-ORIENTING IMAGING DEVICE AND METHODS OF USE

CROSS REFERENCE TO RELATED APPLICATIONS

The present application claims priority to and is a continuation from PCT application serial no. PCT/US2018/012744, filed Jan. 8, 2018, which claims priority to U.S. provisional application Ser. No. 62/443,227, filed Jan. 6, 2017, each herein incorporated by reference in their entireties.

BACKGROUND

Figure 1A:
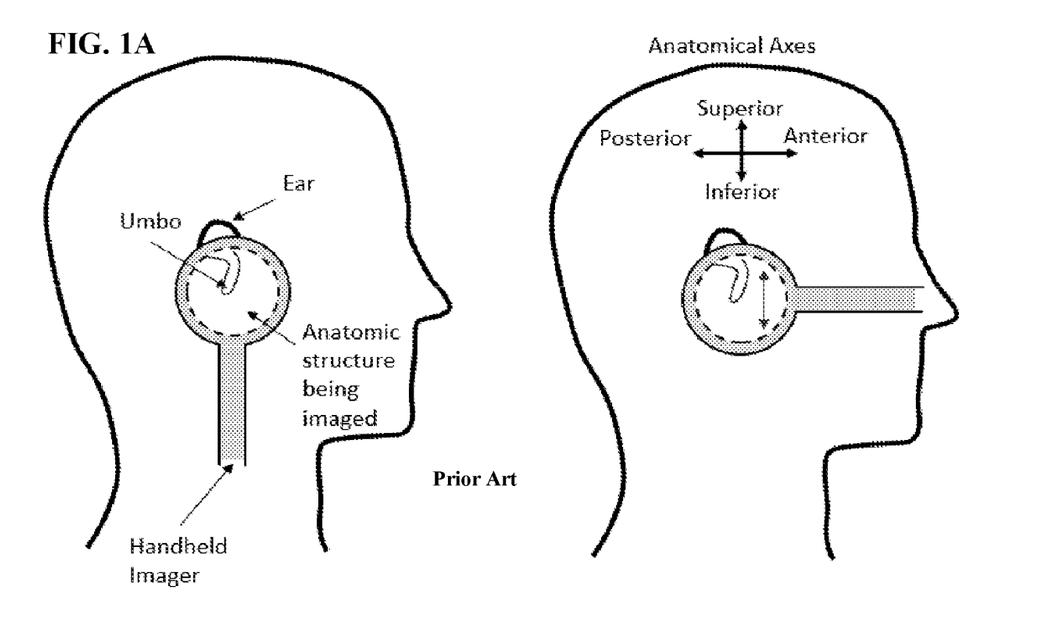
FIGS. 1A-1B is a schematic showing the handheld imager is used to image human eardrum, where the difference in imager orientations generates different images on a standalone display.
Figure 1B:
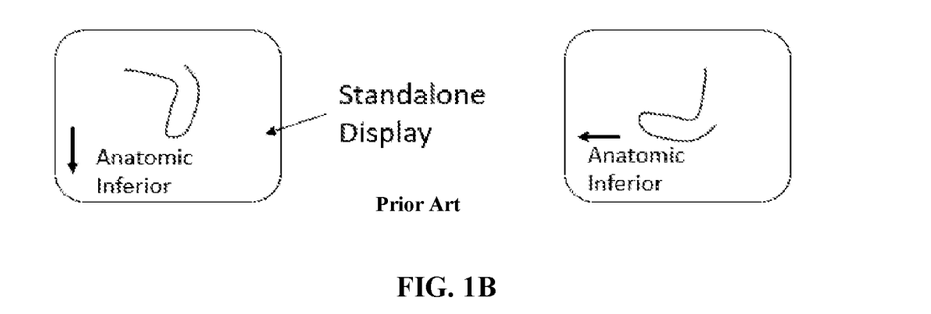

In otoscopic imaging, a handheld imager is commonly used. Different operators handle and position the handheld imager differently referencing the subject's posture. FIG. 1A illustrates the case where the imager is held along the subject superior-inferior axis on the left, as well as a case when it is along the anterior-posterior axis on the right. The dashed circles illustrate the anatomic structure being imaged, which are identical in both cases. When digital imaging technology is used, the captured image is usually displayed on a standalone display, as shown in FIG. 1B. In the example, since the imager is oriented differently, the actual images have 90° rotational difference, as shown in the FIGS. 1A-1B. The difference in orientation can also be easily understood by holding the imager still but "rotate" the subject. A rotated image may create confusion, because the anatomic inferior direction is pointing to the left in the rotated cases.

Things become more confusing when the operator starts to move the imager to locate a region of interest. In the case where the imager is held upright, moving the imager is intuitive. For example, when the operator finds a region of interest on the bottom part of the display, he or she can simply move the imager towards the subject's inferior direction. The reason is that the inferior direction aligns the downward direction of the display. In the 90° rotated scenario, however, if the operator moves the handheld imager inferior to the subject, the image on the display will move left. The operator must adapt the dissociation between the anatomy and image display, which is counter-intuitive and imposes a steep learning curve.

Such confusion exists when the image display is not fixated to the handheld imager.

Imagers can use scanning mechanism and steer the imaging beam to acquire data. The scanning component is fixated to the handheld scanner. The scanning direction is usually pre-determined along one mechanical oscillation axis. By scanning in this pre-determined direction for a certain distance, one can acquire image information along the scan line. By moving or rotating the handheld scanner, one can move the scan line to sample different tissue. However, under certain circumstances, a scan line fixating to the subject anatomy, rather than fixating to the scanner, is more valuable.

For instance, Optical Coherence Tomography (OCT) generates one dimensional image data along the direction of the imaging laser beam. By scanning, a cross-sectional 2D image, or a B-scan, is generated. One axis of the B-scan is depth along the optical beam axis, the other is along the scanning direction. B-scans are commonly used for real time monitoring because OCT imaging speed is sufficiently fast. For otoscopic imaging as shown in FIGS. 1A-1B, scanning along the subject's superior-inferior axis is NOT preferred. The reason is that people's eardrum usually tilts at different angles along this direction. The distance from the tissue to the scanner has more variation. When scanning along the orthogonal anterior-posterior axis, the tissue can be positioned more easily within OCT focal range and imaging range.

The former range determines imaging lateral resolution, while the later prevents the aliasing artifact. There is a need to maintain the anterior-posterior scan regardless of the scanner orientation. There exists a need for a self-orienting imager and/or scanner with which the operator can easily correlate the display image to the subject anatomy.

A secondary need that is general to handheld imager or scanner arises from the highly movable nature. The motion of the handheld device carries information, for instance, that the device may be in use. One can make use of this information of device states. The other aspect is that such a device is subject to hand motion and more likely to be dropped. Detecting handheld device motion can be useful for motion artifact correction or even detection of potential drop.

The present invention attempts to solve these problems as well as others.

SUMMARY OF THE INVENTION

Provided herein are systems, methods and apparatuses for a Self-Orienting Imaging Device and Methods of Use. The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards an area of a subject and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The Self-Orienting Imaging Device and Methods of Use sense the orientation of the handheld imaging, and apply the rotational correction by rotating the image to be displayed. The Self-Orienting Imaging Device and Methods comprises an orientation sensing method and a correction method.

Orientation sensors, such as accelerometer, gyroscope, magnetometer or any combination, can be used for sensing. For example, fusing the data from all accelerometer, gyroscope and magnetometer makes good use of the quick response time and sensitivity of the gyroscope, while the accelerometer and the magnetometer can correct the gyroscope drift over a long period. An accelerometer is an electromechanical device used to measure acceleration forces. Such forces may be static, like the continuous force of gravity or, as is the case with many mobile devices, dynamic to sense movement or vibrations.

When a scanner is used, alternative solution is feasible by adjusting the scanning element in the scanner, such that the eventual scanning direction remains unchanged referencing the subject anatomy. Rather than applying the orientation correction to the displayed image, the self-orienting mechanism can be implemented in the hardware. The additional core technology is a scanning adjustment method.

A 2D scanning element, such as Microelectromechanical Systems (MEMS), piezoelectric device or galvanometer, can be used to adjust directions. These elements can oscillate in two orthogonal directions, driven by independent waveforms. Scanning in an arbitrary direction can be achieved by apply two in-phase waveforms with different amplitudes.

Figures 2A, 2B:
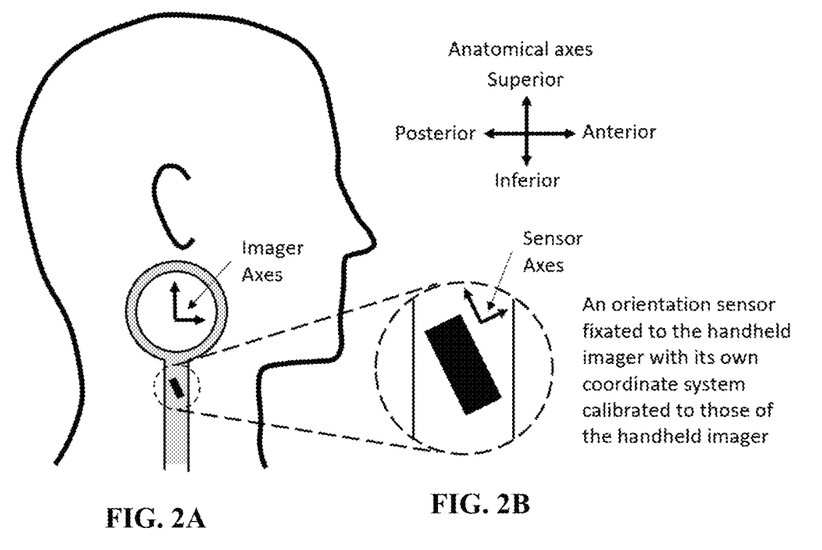
FIG. 2A is a schematic showing the installation of the orientation sensor, where the sensor's axes must be calibrated to those of the imager and only two axes are depicted.
FIG. 2B is enlarged portion of FIG. 2A of the orientation sensor with the sensor axes.
Figure 2C:
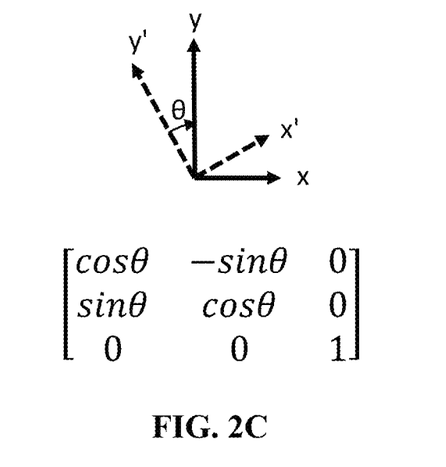
FIG. 2C illustrates an exemplary transformation matrix where the z axes of the scanner and the sensor align and the x-y plane rotates an angle θ.

An illustration of the sensing design is in FIG. 2A. The orientation sensor can be fixated to the handheld scanner, as shown in FIG. 2B. The relative orientation of the sensor with respect to the scanner can be arbitrary, if a calibration is done to register the sensor's axes to those of the scanner. The registration is completed by positioning the scanner in one or a few pre-defined orientations. The corresponding sensor orientation(s) are used to calculate a coordinate transformation matrix. FIG. 2C illustrates an exemplary transformation matrix when the z axes of the scanner and the sensor align and the x-y plane rotates an angle $\theta$.

Figure 3A:
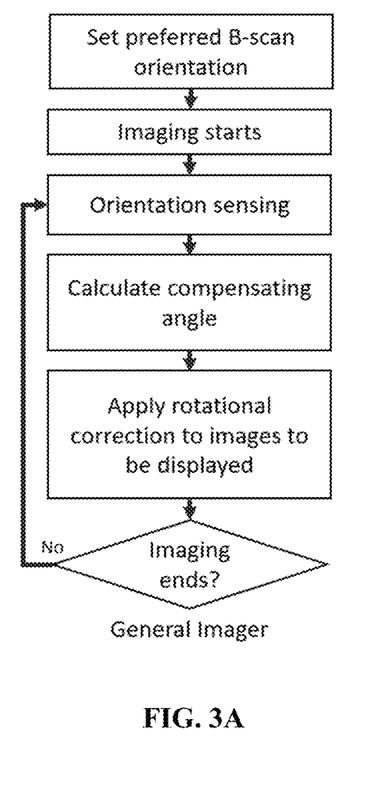
FIG. 3A is a schematic flow chart of the self-orienting work flow when imaging subjects and applies to a general imager.

In one embodiment, the process to image subjects is illustrated in FIG. 3A. First, the handheld device determines a preferred display orientation, which may occur during a calibration step. In one embodiment, the default scanning orientation of the handheld scanner is aligned along the posterior-anterior axis; however, the handheld scanner may be aligned to other axes such as the superior-inferior axis or the left-right axis. Once aligned, the operator triggers a calibration signal so that the scanner records the preferred display orientation. In another embodiment, a software method is employed. The operator will hold the imager still and the software will provide an option to rotate the displayed image to a preferred orientation. This approach is equivalent to the first approach, with less hardware design requirement. Then the operator will start imaging and can handle the scanner in any needed way. The new scanner orientations can be obtained from the orientation sensor. The compensation is calculated by comparing the new and the preferred orientations, which is the rotational angle the software will compensate for. The rotational angle may be any angle within the full 360 degree field. Users hold the device in many different ways, including upside-down. If imaging does not end, the algorithm reroutes back to the orientation sensing step.

Figure 3B:
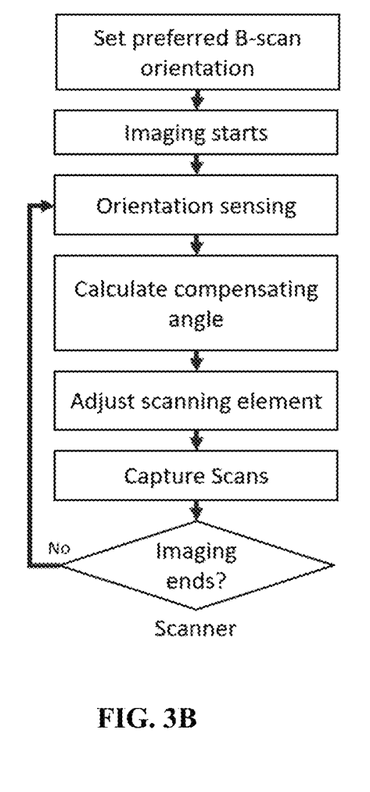
FIG. 3B is a schematic flow chart of the self-orienting work flow when imaging subjects and applies to imager with scanning mechanism.

In the scanning case, the sensor installation will be the same as the general handheld imager embodiment, where the orientation sensor can be fixated to the scanner along any position. Additional hardware configuration will calibrate the scanning angle to the driving waveform requirement. The difference in the self-orienting work flow is to adjust the scanning angle instead of applying the rotation to the display image, as shown in FIG. 3B. The adjustment angle is converted to the driving waveform amplitude of the 2D scanning element. If imaging does not end, the algorithm reroutes back to the orientation sensing step. The adjustment angle may be any angle within the full 360 degree field. Users hold the device in many different ways, including upside-down. The range of the waveform amplitude to be driven is dependent on the type of scanner used.

The Self-Orienting Imaging Device and Methods addresses the need for image orientation invariance when the image display is not fixated to the infrared handheld imager. While a display fixed to the handheld obviates the need for picture-correction, it does not solve the scanning problem. The scanning problem will always need correction. Without correction, the displayed image rotates as the operator changes the orientation of the imager. It creates confusion when navigating the imager or correlating the image to subject anatomy. Maintaining an image orientation, in alignment with subject's posture and regardless of the imaging orientation, provides image consistence and operation convenience. The Self-Orienting Imaging Device and Methods provide a new user experience by self-orienting the displayed image in real time. The Self-Orienting Imaging Device and Methods comprise the identification of an orientation sensor with sufficient sensitivity and a quick response time, a calibration algorithm between the orientations of the sensor and the videoscope, an operating procedure to calibrate the videoscope with the patient, and a software algorithm to apply sensor data to correct for orientation. In the case where scanning mechanism is used, the orientation on a hardware level is compensated. The design requires a calibration procedure correlate the driving waveform to scan angle and a control algorithm to control the scan line to the correct direction.

Similar orientation compensation can be applied to the video otoscope, which can be an additional imaging modality in the OCT scanner.

The Self-Orienting Imaging Device and Methods include an orientation sensor, a scanner and a compensation algorithm. A 2D scanner is not absolutely required. An alternative is a 1D scanner mounted on a rotational actuator, in which case the compensation is done by rotating the actuator.

When one views an upright arrow through otoscope and videoscope, the two figures (FIG. 1A) in the top row show the views through the standard otoscope. The grey shaded area illustrates the otoscope frame, which holds a magnifying glass. The difference between the two cases is that the left otoscope is held upright, while the right one is rotated to an angle θ. One can imagine the images of the arrow through the magnifying glass remains the same regardless of angle θ.

Figure 4A:
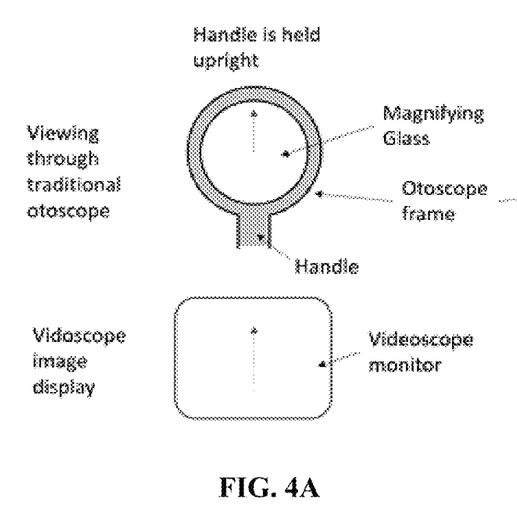
FIGS. 4A-4B are schematic diagrams showing the rotational inconsistency between otoscope and videoscope.
Figure 4B:
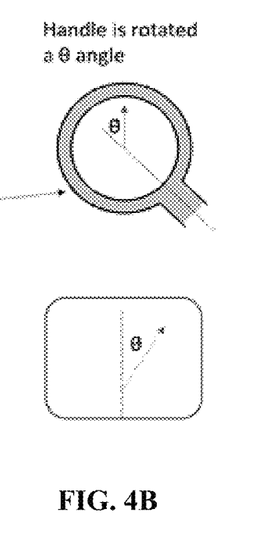

However, when the videoscope is used, the video images are different and counter-intuitive. The reason is that the video camera is fixated to the videoscope handheld frame. When the handle is rotated angle θ counter-clockwise, it is equivalent to hold the camera still and rotate the arrow angle θ clockwise from an imaging perspective. The final image is actually an arrow rotated angle θ clockwise, as shown in the bottom right figure. Not only is the videoscope image different from the standard otoscope (FIG. 4A vs. FIG. 4B), but it also rotates in a counter-intuitive way. The training process can be time-consuming, and the learning experience may be discouraging.

In another embodiment, a motion and/or orientation sensor can also be operably coupled the handheld device to improve usability, device performance and reliability. The motion and/or orientation sensor detects the change of the device state and predicts the next user action. In one embodiment, when someone picks up the handheld device after it stays idle for some time detected by a timer or a real time clock, it is a sign that the device will be used again. The idle period of time may be at least 1 minute. The device motion can be detected by a motion detector and a trigger can be used to wake up hardware peripheral devices. More sophisticated motion patterns can also be used to avoid wake up the system unnecessary. In one embodiment, a "wake-up" trigger can be shaking the handheld device back and forth twice. A motion detector will consider a valid trigger as the acceleration changes in opposite directions multiple times.

When a motion artifact affects device performance, motion detection by a sensor can alert the operator and/or even help the removal of such artifact. A motion artifact occurs with voluntary or involuntary patient movement during image acquisition. The motion alert can be triggered by detecting whether the device angular velocity or acceleration is above the pre-determined threshold. The angular velocity of an object is the rate of change of its angular displacement with respect to time. In one embodiment, the angular velocity threshold is greater than about 0.001 radian per second. The detected motion information can also be used to compensate for the artifact in the acquired data. For instance, motion blurring is a common artifact. Angular velocity detection can be used to calculate the amount of linear motion artifact at the focal plane which can be used for image de-blurring.

When a handheld device is dropped, there will be a sudden change in acceleration when the device hits a hard surface. The device may be damaged. A motion sensor can be used proactively to detect such a violent motion and alert the operator for potential damage.

Using a prescribed motion or gesture of the imaging device may perform commands, such as calibration, scanning, sensing orientation, or correction method. In particular embodiments, the prescribed motions or gestures focuses on an actual path traveled by the device and is a holistic view of a set of points traversed. As an example, motion in the form of an "O" will recognize that the device has traveled in the form of an "O" because in gesture-based input the device focuses on the path traveled during the motion or movement between a beginning point and an endpoint of the gesture (e.g., even though the beginning and endpoints may be the same). This gesture "O" movement may be mapped to particular functions such that when the device recognizes it has traveled along a path to constitute an "O" gesture, it may perform the commands. In particular embodiments, movement of the device intended as a gesture may be recognized as by the device as a gesture by matching a series, sequence or pattern of accelerations of the movement to those defining gestures of a gesture database. On such gesture is switching the device from one ear of the patient to the other ear of the patient.

The proposed solution for self-orientation is to sense the rotation of the videoscope, and apply the rotational angle for digital compensation before the images are displayed. The core technology is to sense and compensate the orientation of videoscope. The proposed solution for usability, performance and reliability improvement is also to sense motion.

A motion sensor, such as Bosch BNO055, can be used for sensing. The sensor consists of accelerometer, gyroscope and magnetometer, from which the data will be fused into stable three-axis orientation output. The orientation references the direction of gravity and Earth's magnetic field. The sensor chip is small enough to be attached to videoscope handheld piece. When used alone, the accelerometer can detect acceleration and the gyroscope can detect angular velocity. In one embodiment, the accelerometer includes a high cross axis sensitivity, where the accelerometer detects disturbances of delta X=0.002, delta Y=0.001, and delta Z=0.000.

In one embodiment, to build a self-oriented videoscope, the orientation sensor chip will be fixated to the videoscope. A calibration algorithm registers the axes of the chip to those of the videoscope during manufacturing, so that the orientation of the sensor chip can be converted to that of the videoscope.

Figure 5:
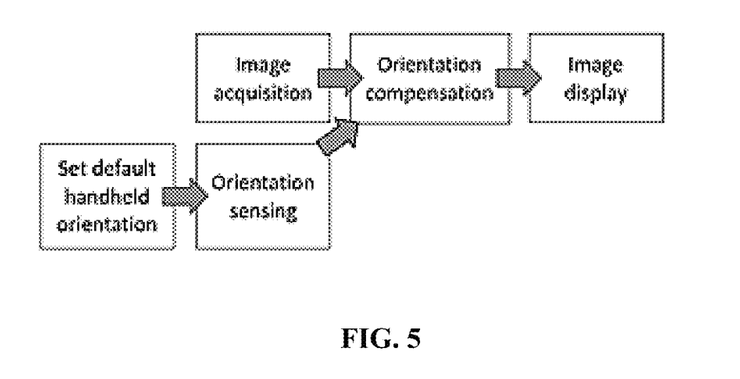
FIG. 5 is a flow chart showing the Orientation compensation process flow.

The process of orientation compensation is illustrated in FIG. 5. As a first step, a default handheld orientation is set in which the image is preferred to be displayed. A natural option is to hold the handle along the human superior-inferior axis with the speculum end pointing superior.

When capturing the videoscope image starts, the new orientation can be obtained from the orientation sensor, and compared to the default orientation. The orientation compensation can be done by applying a reverse rotation to the captured image. Looking at the compensated image will be the same as seeing through the traditional otoscope.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

Software includes applications and algorithms. Software may be implemented in a smart phone, tablet, or personal computer, in the cloud, on a wearable device, or other computing or processing device. Software may include logs, journals, tables, games, recordings, communications, SMS messages, Web sites, charts, interactive tools, social networks, VOIP (Voice Over Internet Protocol), e-mails, and videos.

In some embodiments, some or all of the functions or process(es) described herein and performed by a computer program that is formed from computer readable program code and that is embodied in a computer readable medium. The phrase "computer readable program code" includes any type of computer code, including source code, object code, executable code, firmware, software, etc. The phrase "computer readable medium" includes any type of medium capable of being accessed by a computer, such as read only memory (ROM), random access memory (RAM), a hard disk drive, a compact disc (CD), a digital video disc (DVD), or any other type of memory.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A method of self-orienting an imaging device, comprising: a. Calibrating an orientation of a sensor operably fixed to a scanner or imager; b. Calculating a transformation matrix from the orientation when the z axes of the scanner and the sensor align and the x-y plane rotates an angle $\Theta$; c. Obtaining a preferred display orientation by aligning a default scanning orientation of the scanner along an axis; d. Imaging with the scanner and obtaining new scanner orientations; and e. Comparing the new scanner orientations with the preferred display orientation to determine a rotational angle.

2. The method of claim 1, wherein the default scanning orientation of the scanner is aligned along the posterior-anterior axis.

3. The method of claim 1, wherein the obtaining preferred display orientation comprises holding the scanner stationary and providing an option to rotate a displayed image to a preferred orientation.

4. The method of claim 3, wherein the scanner is a videoscope.

5. The method of claim 4, wherein the scanner is a handheld imager.

6. The method of claim 1, wherein the orientation sensor is selected from the group consisting of accelerometer, gyroscope, magnetometer or any combination thereof.

7. A method of self-orienting an imaging device, comprising: a. Setting a preferred B-scan orientation, fixating an orientation sensor to a scanner and Calibrating a scanning angle of the scanner to drive a waveform requirement and to fulfill a driving waveform requirement; b. Adjusting the scanning angle by an adjustment angle; c. Converting the adjustment angle to drive the waveform requirement of the scanner; and d. Imaging with the scanner.

8. The method of claim 7, further comprising controlling the scan line in the correct direction.

9. The method of claim 8, wherein the adjusting the scanning angle may be accomplished by a MEMS, piezoelectric device, or a galvanometer.

10. A method of self-orienting an imaging device, comprising: a. Detecting a motion of the imaging device by a motion detector and preparing the device for use or translating motion patterns to user commands to the device and Calibrating an orientation of a sensor operably coupled to a scanner; b. Calculating a transformation matrix from the orientation; c. Obtaining a preferred scan orientation; d. Calibrating a scanning angle of a scanner to drive a waveform requirement to fulfill a driving waveform requirement; e. Adjusting the scanning angle by an adjustment angle; f. Converting the adjustment angle to drive the waveform requirement; and g. Imaging with the scanner.

11. The method of claim 10, wherein the adjusting the scanning angle may be accomplished by a MEMS, piezoelectric device, or a galvanometer.

12. The method of claim 10, wherein the imaging device is an Optical Coherence Tomography imaging device.

13. The method of claim 10, further comprising detecting a motion artifact by a sensor; and triggering a motion alert by detecting whether the device angular velocity or acceleration is above a pre-determined threshold.

14. The method of claim 10, further comprising detecting a gesture of the imaging device by a motion detector and using the gesture of the imaging device to perform commands selected from the group of calibration, scanning, sensing orientation, and a correction method.

15. The method of claim 1, further comprising detecting a motion artifact by a sensor; and triggering a motion alert by detecting whether the device angular velocity or acceleration is above a pre-determined threshold.

16. The method of claim 7, further comprising detecting a motion artifact by a sensor; and triggering a motion alert by detecting whether the device angular velocity or acceleration is above a pre-determined threshold.

* * * * *